United States Patent [19]

Drake

[11] Patent Number: 4,596,783

[45] Date of Patent: Jun. 24, 1986

[54] HYDROGENATION CATALYSTS AND SELECTIVE HYDROGENATION THEREWITH

[75] Inventor: Charles A. Drake, Bartlesville, Okla.

[73] Assignee: Phillips Petroleum Company, Bartlesville, Okla.

[21] Appl. No.: 780,749

[22] Filed: Sep. 27, 1985

Related U.S. Application Data

[62] Division of Ser. No. 684,399, Dec. 20, 1984.

[51] Int. Cl.$^4$ ............................................. B01J 31/04
[52] U.S. Cl. ..................................... 502/167; 502/170
[58] Field of Search ................................. 502/167, 170

[56] References Cited

U.S. PATENT DOCUMENTS 3,192,168  6/1965  Grenet .................................. 502/170
3,641,113  2/1972  Fernholz et al. ............... 502/167 X

FOREIGN PATENT DOCUMENTS 40829  12/1981  European Pat. Off. ............ 570/216
883481  11/1961  United Kingdom ................ 570/216

Primary Examiner—Patrick P. Garvin
Attorney, Agent, or Firm—Stephen E. Reiter

[57] ABSTRACT

Selective hydrogenation process is provided employing as catalyst a composition consisting essentially of elemental palladium on calcium carbonate support with lead acetate and an aromatic amine oxide. Very high selectivities to cis-olefinic compounds from acetylenic compounds is achieved employing the catalyst of the invention.

3 Claims, No Drawings

HYDROGENATION CATALYSTS AND SELECTIVE HYDROGENATION THEREWITH

This application is a division of application Ser. No. 684,399, filed Dec. 20, 1984.

BACKGROUND

This invention relates to hydrogenation catalysts and hydrogenation therewith. In another aspect, the present invention relates to hydrogenation of acetylenic compounds. In a further aspect, the invention relates to the stereospecific hydrogenation of acetylenic compounds.

The selective hydrogenation of acetylenic compounds to cis-olefinic compounds can be accomplished with a variety of prior art catalysts. However, while selectivity to the cis-olefinic product of greater than 90% can often be achieved with known catalysts, the concomitant formation of several percent of trans-olefinic compounds and saturated aliphatic compounds as reaction by-products is undesirable for many end uses. In addition, high selectivities to cis-olefinic products is sometimes achieved by carrying out the reaction under low temperature conditions which are expensive to maintain and require long reaction times in order to achieve high conversion levels of starting material. Conversely, when highly reactive catalysts are employed, selectivity to the desired cis-olefinic products frequently suffer.

OBJECTS OF THE INVENTION

An object of the present invention is, therefore, a process to hydrogenate acetylenic compounds with high selectivity to cis-olefinic compounds in high yield.

Another object of the invention is a hydrogenation catalyst capable of selectively hydrogenating acetylenic compounds.

These and other objects of the invention will become apparent from the disclosure and claims herein provided.

STATEMENT OF THE INVENTION

In accordance with the present invention, I have discovered that the selectivity of hydrogenation of acetylenic compounds to cis-olefinic compounds with a catalyst consisting essentially of palladium on calcium carbonate modified with lead acetate can be greatly improved by the addition to the catalyst of an aromatic amine oxide. As employed herein, the term "aromatic amine oxide" is intended to include aromatic compounds wherein the N-atom is incorporated as part of an aromatic ring. The term is not, however, intended to include amino-substituted aromatic compounds.

In accordance with another embodiment of the present invention, I have discovered novel catalyst compositions consisting essentially of elemental palladium supported on calcium carbonate with lead acetate and aromatic amine oxide.

DETAILED DESCRIPTION OF THE INVENTION

In accordance with the present invention, a process for the selective conversion of acetylenic compounds to cis-olefinic compounds is provided comprising contacting an acetylenic compound under hydrogenation conditions with hydrogen and a catalyst consisting essentially of elemental palladium on calcium carbonate modified with lead acetate and an aromatic amine oxide.

In accordance with another embodiment of the present invention, novel catalyst compositions consisting essentially of elemental palladium supported on calcium carbonate with lead acetate and an aromatic amine oxide are provided.

The catalysts of the present invention consist essentially of elemental palladium on calcium carbonate support modified with lead acetate and an aromatic amine oxide. The proportion of elemental palladium combined with the calcium carbonate support can vary appreciably, but generally the support contains at least about 0.1% by weight of elemental palladium, based on the total weight of support plus elemental palladium. Generally the support will contain an upper limit of about 10% by weight of elemental palladium, based on the total weight of support plus elemental palladium. Amounts of about 0.5 to about 5 percent by weight of elemental palladium, based on the total weight of support plus elemental palladium are preferred.

Lesser amounts, i.e., about 0.5 wt. % of elemental palladium are preferred when hydrogenation reaction is to be carried out in the continuous mode, while greater amounts, i.e., about 5 wt.% elemental palladium are preferred when the hydrogenation reaction is to be carried out in the batch mode.

The amount of lead acetate employed to modify the palladium on calcium carbonate catalyst can vary within wide ranges. In order to provide additional guidance, the following values are suggested (calculated as the weight ratio of elemental lead to elemental palladium):

|  | Pb/Pd Wt Ratio |
| --- | --- |
| Broad | 1–10:1 |
| Intermediate | 1.5–5:1 |
| Preferred | 2–3:1 |

Aromatic amine oxides employed in the practice of the present invention conform to the formulae:

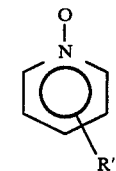

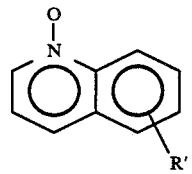

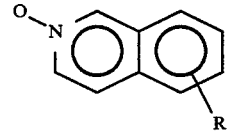

and mixtures of any two or more thereof, wherein R' is H, or $C_1$–$C_4$ alkyl. Aromatic amine oxides which satisfy the above formulae include pyridine N-oxide, quinoline N-oxide, 2-methylpyridine N-oxide and the like. Pyridine N-oxide is presently preferred because of its ready availability and established effectiveness.

While the amount of aromatic amine oxide employed in the practice of the present invention can vary broadly, the following values are provided for additional guidance. The ratios expressed below are expressed in terms of weight ratio of the aromatic amine oxide relative to the weight of elemental palladium:

| | Aromatic Amine oxide/Pd wt. ratio |
|---|---|
| Broad | 1–20:1 |
| Intermediate | 2–10:1 |
| Preferred | 2.5–5:1 |

Acetylenic compounds contemplated to be within the scope of the present invention include acetylenic compounds having from four up to about thirty carbon atoms and at least one non-terminal carbon-carbon triple bond. Compounds which satisfy these criteria can be represented by the formula:

$$R-C\equiv C-R$$

wherein each R is independently a $C_1$–$C_{20}$ carbon radical, with the proviso that the total molecule not exceed about 30 carbon atoms. Preferred acetylenic compounds for use in the practice of the present invention may contain at least one functional group selected from the group consisting of:

—Cl,

—Br,

—I,

—CHO,

—$CO_2R''$, and the like, wherein each R'' is independently a $C_1$–$C_{10}$ carbon radical, because prior art selective hydrogenation reactions in the presence of such functional groups have been found to be particularly difficult. Thus, an especially preferred acetylenic compound for use in the practice of the present invention can be represented by the formula:

$$H-(CH_2)_x-C\equiv C-C-(CH_2)_y-CH_2-X$$

wherein X represents any one of the functional groups recited above, x is 1–20, inclusive and y is 0–20, inclusive, with the proviso that the total molecule not exceed about 30 carbon atoms.

When carrying out the hydrogenation reaction of the present invention, the ratio of acetylene substrate to elemental palladium can vary widely. In order to provide additional guidance, the following ratios are suggested:

| | Moles acetylenic substrate/mole Pd° |
|---|---|
| Broad | 50–2000:1 |
| Intermediate | 100–1000:1 |
| Preferred | 200–500:1 |

Reaction parameters suitable for the practice of the present invention include a preferred reaction pressure of about 50 up to about 300 psig, although almost any pressure can be employed. Suitable reaction temperatures include about 0° C. up to about 100° C. with temperature preferably maintained between about 20° and about 50° C. Reaction time can broadly be 30 minutes up to about 8 hours, with about 60 minutes to about 120 minutes preferred.

While not necessary for the practice of the present invention, it is convenient to carry out the inventive hydrogenation reaction with catalyst suspended in a suitable solvent, such as for example, saturated hydrocarbon solvents with about 5 to 12 carbon atoms. Solvent and substrate can be employed in any suitable ratio as readily determined by those of skill in the art. Suitable ratios are about 10 to 1 to about 1 to 10 parts by volume of solvent to substrate. Preferably, for ease of handling and product recovery, solvent and substrate are charged to the reactor in roughly equal volumes.

Hydrogen is generally fed on demand, i.e., as it is taken up by the reaction mixture. Thus, for example, where reaction is carried out at 120 psig, reactor pressure may be allowed to drop to about 60 psig, then the pressure will be returned to about 120 psig by introducing more hydrogen. Alternatively, reaction may be run at atmospheric pressure with continuous hydrogen uptake from a manometer assembly as hydrogen is consumed by the reaction.

Reaction workup consists of catalyst removal, for example, by filtration, and solvent removal by such techniques as flash distillation.

A further understanding of the present invention and its advantages will be provided by reference to the following non-limiting examples.

EXAMPLES

Commercially available Lindlar catalyst (5% palladium on calcium carbonate modified with about 14 wt % lead acetate; catalyst #D136 from Englehard Corp., Newark, N.J.) and 50 grams of 11-hexadecynyl bromide in 70 g of hexane were contacted under about 100 psig of hydrogen pressure at about 30° C. for 0.5–1.5 hours, in the presence or absence of added catalyst modifier. Results of several hydrogenation reactons are summarized in the Table.

TABLE

| | Reagents, g | | Reaction time, h | Product Analysis, %** | | |
|---|---|---|---|---|---|---|
| Run | Catalyst* | Modifier | | Z-11 | E-11 | Saturate |
| 1 (Control) | 1.0 | None | 0.5 | 87.9 | 9.1 | 2.9 |
| 2 (Control) | 0.7 | Pyridine, 0.05 | 1.0 | 96.8 | 2.2 | 1.0 |
| 3 (Invention) | 0.7 | Pyridine N-oxide, 0.05 | 1.5 | 97.2 | 1.5 | 0.8 |
| 4 (Invention) | 1.0 | Pyridine N-oxide, 0.1 | 1.0 | 97.4 | 1.8 | 0.9 |

*Unmodified Lindlar catalyst (5% $Pd/CaCO_3$ + $Pb(OAc)_2$)
**Z-11 is cis-olefinic product (Z-11-hexadecenyl bromide)
E-11 is trans-olefinic product (E-11-hexadecenyl bromide)
Saturate is saturated product (hexadecyl bromide)

The results in the Table demonstrate that an aromatic amine oxide such as pyridine N-oxide is a superior modifier for use with hydrogenation catalysts consisting essentially of palladium on calcium carbonate support modified with lead acetate. Excellent selectivities to the desired cis-olefinic product are obtained in the presence of the inventive modifier.

Thus, while a commercially available Lindlar catalyst gave 92.5% selectivity to Z-11-hexadecenyl bromide from 11-hexadecynyl bromide, inventive catalyst containing small amounts of the aromatic amine oxide, pyridine N-oxide, gave nearly 98% selectivity to Z-11-hexadecenyl bromide.

The examples have been provided to illustrate the practice of my invention and should not be read so as to limit the scope of my invention or the appended claims in any way. Reasonable variation and modification, not departing from the essence and spirit of my invention are contemplated to be within the scope of patent protection desired and sought.

That which is claimed:

1. A catalyst composition consisting essentially of elemental palladium on a calcium carbonate support with lead acetate and an aromatic amine oxide, wherein said palladium is present in an amount of about:

0.1–10 wt % elemental palladium based on total weight of palladium and calcium carbonate support;

wherein the weight ratio of lead, calculated as the element, to elemental palladium, is 1–10:1;

wherein the weight ratio of aromatic amine oxide to elemental palladium is about 1–20:1; and wherein said aromatic amine oxide has from about 5 to about 18 carbon atoms per molecule and is selected from the group consisting of:

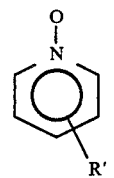

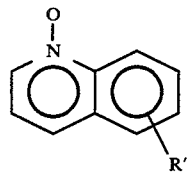

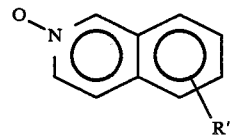

and mixtures of any two or more thereof, wherein R' is H or $C_1$–$C_4$ alkyl.

2. A composition in accordance with claim 1 wherein said palladium is present in an amount of about 0.5–5 wt % elemental palladium based on total weight of palladium and calcium carbonate support;

wherein the weight ratio of lead to elemental palladium is 1.5–5:1; and wherein the weight ratio of aromatic amine oxide to elemental palladium is about 2–10:1.

3. A composition in accordance with claim 1 wherein said aromatic amine oxide is pyridine N-oxide.

* * * * *